United States Patent [19]
Vari et al.

[11] Patent Number: 5,701,902
[45] Date of Patent: Dec. 30, 1997

[54] SPECTROSCOPIC BURN INJURY EVALUATION APPARATUS AND METHOD

[75] Inventors: Sandor G. Vari, Woodland Hills; Jean-Michel I. Maarek, Rancho Palos Verdes, both of Calif.

[73] Assignee: Cedars-Sinai Medical Center, Los Angeles, Calif.

[21] Appl. No.: 306,118

[22] Filed: Sep. 14, 1994

[51] Int. Cl.$^6$ ........................................... A61B 5/00
[52] U.S. Cl. ........................................... 128/664; 128/665
[58] Field of Search ........................................... 128/633, 634, 128/664, 665

[56] References Cited

U.S. PATENT DOCUMENTS

| | | | |
|---|---|---|---|
| 3,313,290 | 4/1967 | Chance et al. | 128/2 |
| 3,614,414 | 10/1971 | Gores | 240/2 |
| 3,709,612 | 1/1973 | Clemens | 356/178 |
| 3,830,222 | 8/1974 | Chance | 128/2 A |
| 3,975,098 | 8/1976 | West | 356/85 |
| 4,162,405 | 7/1979 | Chance et al. | 250/461 B |
| 4,170,987 | 10/1979 | Anselmo et al. | 128/665 |
| 4,178,917 | 12/1979 | Shapiro | 128/665 |
| 4,184,175 | 1/1980 | Mullane, Jr. | 358/93 |
| 4,236,526 | 12/1980 | Richard | 128/633 |
| 4,412,543 | 11/1983 | Vassiliadis et al. | 128/633 |
| 4,449,535 | 5/1984 | Renault | 128/634 |
| 4,479,499 | 10/1984 | Alfano | 128/665 |
| 4,510,938 | 4/1985 | Jobsis et al. | 128/633 |
| 4,569,354 | 2/1986 | Shapiro et al. | 128/665 |
| 4,608,990 | 9/1986 | Elings | 128/633 |
| 4,629,693 | 12/1986 | Khanna | 435/7 |
| 4,631,413 | 12/1986 | Jensen et al. | 250/458.1 |
| 4,675,529 | 6/1987 | Kushida | 250/458.1 |
| 4,894,547 | 1/1990 | Leffell et al. | 250/461.2 |
| 4,930,516 | 6/1990 | Alfano et al. | 128/665 |
| 4,957,114 | 9/1990 | Zeng et al. | 128/665 |
| 4,979,900 | 12/1990 | Okamoto et al. | 433/224 |
| 4,981,138 | 1/1991 | Deckelbaum et al. | 128/665 |
| 5,001,054 | 3/1991 | Wagner | 435/14 |
| 5,014,707 | 5/1991 | Schwarz et al. | 128/633 |
| 5,034,189 | 7/1991 | Cox et al. | 422/52 |
| 5,036,853 | 8/1991 | Jeffcoat | 128/634 |

(List continued on next page.)

FOREIGN PATENT DOCUMENTS

| | | |
|---|---|---|
| 2 539 613 | 7/1984 | France . |
| 227 044 A1 | 9/1985 | Germany . |
| 227044 | 9/1985 | Germany ........................... 268/291.6 |
| 37 18202 C1 | 11/1988 | Germany . |
| 40 31 320 A1 | 4/1992 | Germany . |
| 2 254 417 | 10/1992 | United Kingdom . |
| WO 90/10219 | 9/1990 | WIPO . |
| WO 90/13091 | 11/1990 | WIPO . |
| WO 91/12766 | 9/1991 | WIPO . |
| WO93/01745 | 2/1993 | WIPO . |

OTHER PUBLICATIONS

Herndon et al., "Management of the Pediatric Patient With Burns," J. of Burn Care & Rehab., Feb. 1993, pp. 3–8.

(List continued on next page.)

Primary Examiner—Ruth S. Smith
Attorney, Agent, or Firm—Pretty, Schroeder & Poplawski

[57] ABSTRACT

A burn evaluation apparatus and related method, that allows a surgeon to make a quick evaluation of the extent and depth of a skin burn injury by employing induced ultraviolet or blue light fluorescence spectroscopy and visible and infrared reflectance spectroscopy. The apparatus monitors the condition of the structural and metabolic constituents in the injured skin. The apparatus includes a plurality of light sources, a sensor, a microprocessor, and several optical fiber bundles. The light sources emit excitation light at predetermined wavelengths, and when each is activated, the sensor measures the amount return light received within several wavelength bands of interest. A side fiber bundle spaced about a centimeter from a main fiber bundle assists in detecting tissue water below the burn area. By optically evaluating the skin at the burn site, the apparatus prevents the unnecessary removal of viable skin that will heal spontaneously within a few weeks, thereby reducing the amount of skin that must be surgically grafted.

15 Claims, 11 Drawing Sheets

U.S. PATENT DOCUMENTS

| | | | |
|---|---|---|---|
| 5,037,738 | 8/1991 | Lamos et al. | 435/12 |
| 5,042,494 | 8/1991 | Alfano | 128/665 |
| 5,046,501 | 9/1991 | Crilly | 128/665 |
| 5,072,731 | 12/1991 | Taratuta et al. | 128/633 |
| 5,074,306 | 12/1991 | Green et al. | 128/664 |
| 5,093,266 | 3/1992 | Leader et al. | 436/68 |
| 5,115,137 | 5/1992 | Andersson-Engels et al. | 250/461.2 |
| 5,127,405 | 7/1992 | Alcala et al. | 128/633 |
| 5,172,693 | 12/1992 | Doody | 128/633 |
| 5,217,456 | 6/1993 | Narciso, Jr. | 606/15 |
| 5,413,108 | 5/1995 | Alfano | 128/665 |
| 5,452,723 | 9/1995 | Wu et al. | 128/665 |

OTHER PUBLICATIONS

Housinger et al., "*Ordering of Laboratory Work in the Management of Pediatric Burn Patients: Technical Note,*" J. of Trauma, vol. 34, No. 1, Jan. 1993, pp. 139–141.

Trop et al., "*Core Body Temperature Responses Immediately After Cutaneous Thermal Injury in Rats,*" J. of Burn Care & Rehab., vol. 13, No. 6, Dec. 1992, pp. 632–638.

Schweizer et al., "*Noninvasive Assessment of Metabolism in Wounded Skin by $^{31}P$-NMR in Vivo.*" J. of Trauma, vol. 33, No. 6, Dec. 1992, pp. 828–834.

Ryan et al., "*Increased Gut Permeability Early After Burns Correlates with the Extent of Burn Injury,*" Critical Care Medicine, vol. 20, No. 11, Nov. 1992, pp. 1508–1512.

Tomera et al., "*Mod. of Calcium Flux of Twitch Skeletal Muscle in Mice Subj. to 20 Body Surface Area Burn,*" J. Burn Care & Rehab., vol. 15, No. 5, Oct. 1992, pp. 546–555.

Lawrence, C., "*Hematologic Changes in Massive Burn Injury,*" Critical Care Medicine, vol. 20, No. 9, Sep. 1992, pp. 1284–1288.

Biswas, D.R., "*Optical Fiber Coatings for Biomedical Applications,*" Optical Engineering, vol. 31, No. 7, Jul. 1992, pp. 1400–1403.

Green et al., "*Burn Depth Estimation Using Indocyanine Green Fluorescence,*" Arch Dermatol, vol. 128, Jan. 1992, pp. 43–49.

Bassnett et al., "*Intracellular pH Measurement Using Single Excitation–Dual Emission Fluorescence Ratios,*" American Journal of Physiology, 1990, pp. C171–C178.

Mendelson et al., "*Blood Glucose Measurement by Multiple Attenuated Total Reflection & Infrared Absorption Spectroscopy,*" IEEE Trans. on Biomedical Engr., vol. 37, No. 5, May 1990, pp. 458–464.

Pini et al., "*Laser Dentistry: Root Canal Diagnostic Technique Based on Ultraviolet–Induced Fluorescence Spectroscopy,*" Lasers in Surgery & Medicine, vol. 9, 1989, pp. 358–361.

Afromowitz et al., "*Multispectral Imaging of Burn Wounds: A New Clinical Instrument for Evaluating Burn Depth,*" IEEE Trans. on Biomedical Engr., vol. 35, No. 10, Oct. 1988, pp. 842–849.

Afromowitz et al., "*Clinical Evaluation of Burn Injuries Using an Optical Reflectance Technique,*" IEEE Trans. on Biomedical Engr., vol. 34, No. 2, Feb. 1987, pp. 114–127.

Moneta et al., "*Infrared Fluorescence Videomicroscopy of Skin Capillaries with Indocyanine Green,*" Int. J. Microcirc. Clin. Exp., pp. 25–34, 1987.

Gatti et al., "*Evaluation of the Burn Wound with Perfusion Fluorometry,*" Journal of Trauma, vol. 23, No. 3, Mar. 1983, pp. 202–206.

"*Substance Identification Neural Network,*" Physical Optical Corp. product information, Date: unknown.

Andersson et al., "*Remote Sample Characterization Based on Fluorescence Monitoring,*" Appl. Phys., vol. B44, No. 1, Sep. 1987, pp. 20–28, Berlin, W. Germany.

Heimbach et al., "*Burn Depth Estimation—Man or Machine,*" Journal of Trauma, vol. 24, No. 5, 1984, pp. 373–378.

Anselmo et al., "*Infrared Photography as a Diagnostic Tool for the Burn Wound,*" Proceedings of the Society of Photo–Optical Instrumentation Engineers, vol. 40, Aug. 1973, pp. 181–188.

Anselmo et al., "*Multispectral Photographic Analysis,*" Annals of Biomedical Engineering, vol. 5, No. 2, Jun. 1977, pp. 179–193.

Anselmo et al., "*Diagnosis of Cutaneous Thermal Burn Injuries by Multispectral Imaging Analysis,*" Jet Propulsion Laboratory Publication 79–34, Sep. 1978, pp. i–8–2.

Katsura et al., "*Untraviolet Absorption of Human Teeth as Revealed by Microphotometry,*" ACTA Histochem Cytochem, vol. 7, No. 4, 1974, pp. 328–333.

Horibe et al., "*Multiple Distribution of the Fluorescence in Human Teeth,*" ACTA Histochem, Cytochem. vol. 7, No. 4, 1984, pp. 334–341.

SPECTROSCOPIC BURN INJURY EVALUATION APPARATUS AND METHOD

BACKGROUND OF THE INVENTION

This invention relates generally to the evaluation of burn injuries and, more particularly, to apparatus, and related methods, that evaluate a burn injury using ultraviolet or visible light fluorescence spectroscopy and infrared absorption spectroscopy of skin tissue at the site of the burn injury.

Figure 1:
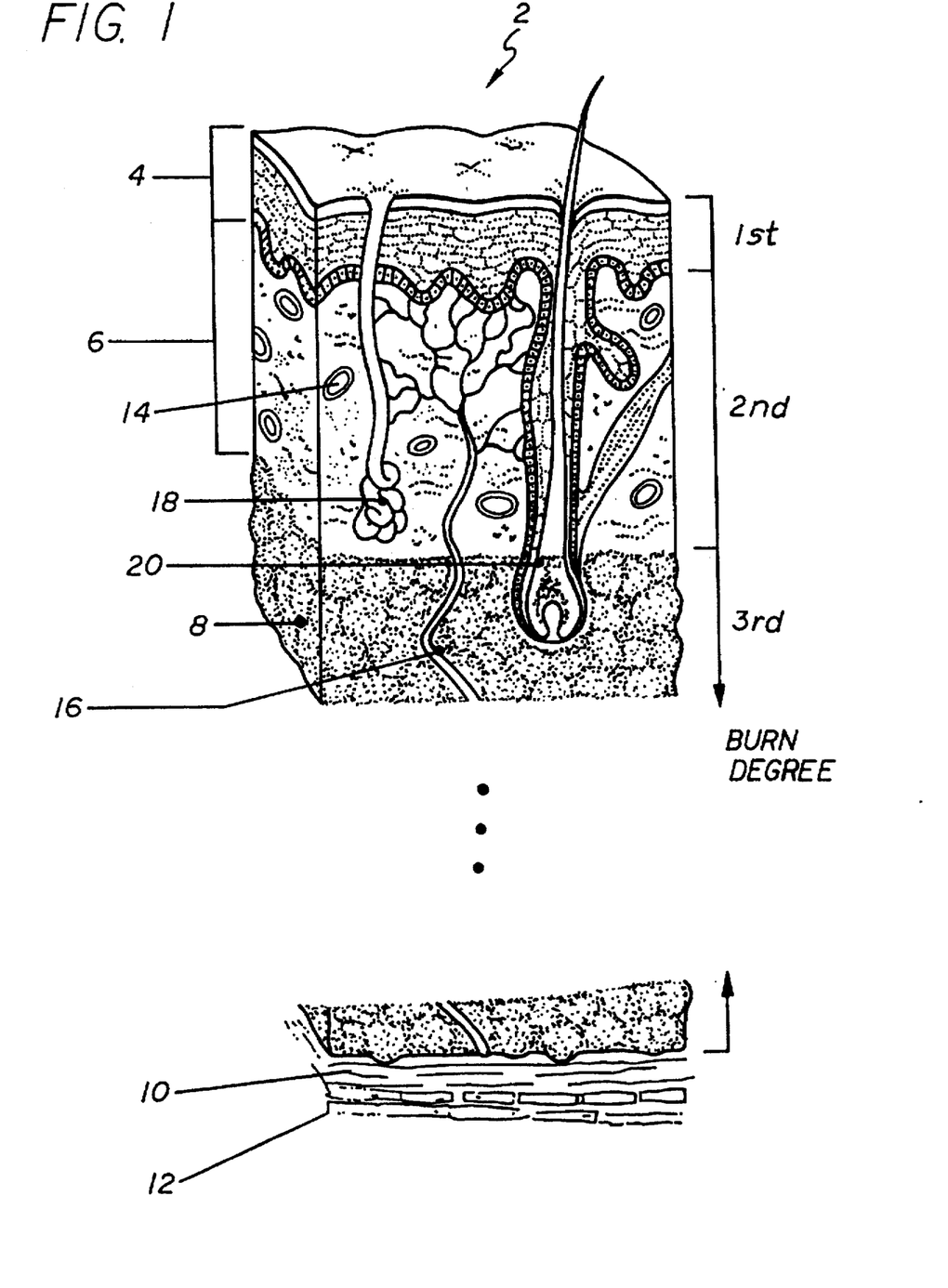
FIG. 1 is a perspective view of a cross-section of human skin.

As shown in FIG. 1, the skin 2 is composed of a thin outer layer 4 (the epidermis) and a thicker inner layer 6 (the dermis). Beneath the dermis is subcutaneous tissue 8, which contains mostly fat, and eventually the muscle fascia 10 and muscle 12. The epidermis forms a tough, waterproof protective coating having tough dead cells on its outside surface that are continually worn away and having living cells on its inner most parts that replace the worn away dead cells. The dermis is living tissue that includes blood vessels 14, nerves 16, sweat glands 18, and hair follicles 20.

Heating of the skin 2, however brief, can cause damage to the cells of its living tissue. Such damage typically is referred to as a burn. Generally, burns can be categorized into degrees that indicate the depth of the burn injury. First degree burns cause reddening of the skin and affect only the epidermis 4. Such burns heal quickly, but the damaged skin may peel away after a day or two. A "sunburn" is an example of a first degree burn. A second degree burn damages the skin more deeply, extending into the dermis 6 and usually causes blisters. However, some of the dermis is left to recover. A third degree burn destroys the full thickness of the dermis and, if the burn is very deep, muscles 12 and bones may be exposed.

Experience has shown that second degree superficial dermal (or partial-thickness) burns will normally heal spontaneously within two weeks with minimal scarring, whereas second degree deep dermal and third degree (or full-thickness) burns usually results in necrotic skin and the resulting wound heals very slowly. Prompt surgical removal of full-thickness burned skin down to the muscle fascia 10 with immediate wound closure using grafts of healthy skin 2 decreases mortality and shortens the hospital stay.

To conserve surface and subjacent skin 2 during surgery, areas of skin that normally will heal spontaneously should be differentiated from areas of skin having more severe burns which will not heal within two weeks and, therefore, require surgical excision and grafting. However, slight changes in burn depth, on the order of fractions of a millimeter, can mean the difference between a burn that will heal spontaneously and a burn that must undergo grafting.

One critical condition that divides necrotic tissue from viable tissue is the circulation of blood through the burn site. Vascular stasis is a condition that typically is an early indicator of eventual tissue necrosis. Clinical criteria utilized to distinguish burn depth, including sensitivity to pin-prick, visual appearance, and viable cutaneous circulation, generally do not reliably identify zones of viable tissue. In addition, techniques such as passive infrared thermography, false-positive images, and high-frequency ultrasound have proven ineffective in assisting surgeons in estimating the depth of burn damage. Without reliable means for evaluating the extent of a burn injury, it is often necessary for the surgeon to excise the entire area of burned skin 2 and subcutaneous tissue 8 down to muscle fascia 10. Such a procedure may sacrifice significant amounts of viable skin.

More successful techniques have been attempted that use fluorescent drugs, such as indocyanine green and fluorescein, applied intravenously and detected with a fiber-optic instrument. However, the fluorescent drugs are slow to reach the burn site and may linger at the burn site, limiting the frequency of testing. Optical reflectance techniques that measure the ratio of reflected green and red light to infrared light using a fiber-optic instrument have had a measure of success in differentiating between full-thickness and partial-thickness burns. However, this technique has required bulky and complex optical instruments and has not been widely adopted clinically.

From the discussion above, it should be apparent that there is a need for a burn detection apparatus and method that rapidly evaluates the extent of a skin burn injury in a reliable and cost-effective manner. The present invention addresses this need.

SUMMARY OF THE INVENTION

The present invention is embodied in a burn classification apparatus, and related method, that employs induced fluorescence spectroscopy and infrared reflectance spectroscopy to monitor the condition of the injured skin. The apparatus assists the surgeon in evaluating the viability of the skin tissue at the site of a burn injury and potentially reduces the occurrence of unnecessary skin grafts.

The apparatus includes a plurality of light sources, a sensor, and a processor. Each light source is adapted to emit excitation light, having a predetermined wavelength, that is directed at the burn site to produce return light. At least one light source of the apparatus is characterized by a wavelength of sufficient energy to cause fluorescence of certain chemical constituents in the skin. The return light includes some of the fluorescent light produced by constituents present within the skin. The sensor, responsive to the return light corresponding to each light source, monitors the return light and generates a plurality of electrical signals based on the intensity of return light within predetermined wavelength bands. The processor is associated with the sensor and processes the plurality of electrical signals so as to determine the condition of the skin at the site of the burn injury.

In a more detailed feature of the invention, the plurality of light sources include a first light source that emits narrow band excitation light having a wavelength between 300 nanometers and 480 nanometers. More specifically, the plurality of light sources includes a first light source that emits excitation light having a wavelength of 405 nanometers, a second light source that emits excitation light having a wavelength of 452 nanometers, a third light source that emits excitation light having a wavelength of 775 nanometers, a fourth light source that emits excitation light having a wavelength of 810 nanometers, a fifth light source that emits excitation light having a wavelength of 904 nanometers, and a sixth light source that emits excitation light having a wavelength of 980 nanometers. Further, each of the plurality of light sources includes a diode laser that generates the respective excitation light.

In another more detailed feature of the invention, the predetermined wavelength bands include a first wavelength band between 450 and 460 nanometers, a second wavelength band between 480 and 490 nanometers, a third wavelength band between 520 and 530 nanometers, a fourth wavelength band between 550 and 560 nanometers, a fifth wavelength band between 770 and 780 nanometers, a sixth wavelength band between 805 and 815 nanometers, a seventh wavelength band between 900 and 910 nanometers, and an eight wavelength band between 970 and 990 nanometers.

The wavelength bands are selected based on the wavelength of the respective excitation wavelengths and are selected in accordance with the selected excitation wavelengths.

In yet another more detailed feature of the invention, the apparatus includes a first optical fiber bundle that has a plurality of excitation optical fibers. The excitation optical fibers are associated with the plurality of light sources in order to transmit excitation light from the respective light source to the site of the burn injury. The first optical fiber bundle also has one or more return optical fibers that transmit the return light from the site of the burn injury to the sensor. Further, the apparatus can include a second optical fiber bundle of one or more optical fibers located at a distance of approximately one centimeter from the first optical fiber bundle during the evaluation of the burn injury. The second optical fiber bundle collects return light to evaluate tissue water below the skin.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENTS

As shown in the exemplary drawings, the present invention is embodied in a burn evaluation apparatus 30, and related method, that allows a surgeon to make a quick evaluation of the extent and depth of a burn injury to the skin. More specifically, the burn classification apparatus employs induced ultraviolet or blue light fluorescence spectroscopy and infrared (IR) reflectance spectroscopy to monitor the condition of the structural and metabolic compounds in the injured skin allowing evaluation of the potential viability of the skin at the burn site. The apparatus helps prevent the unnecessary removal of viable skin that will heal spontaneously within a few weeks, thereby reducing the amount of skin that must be surgically grafted.

Figure 2:
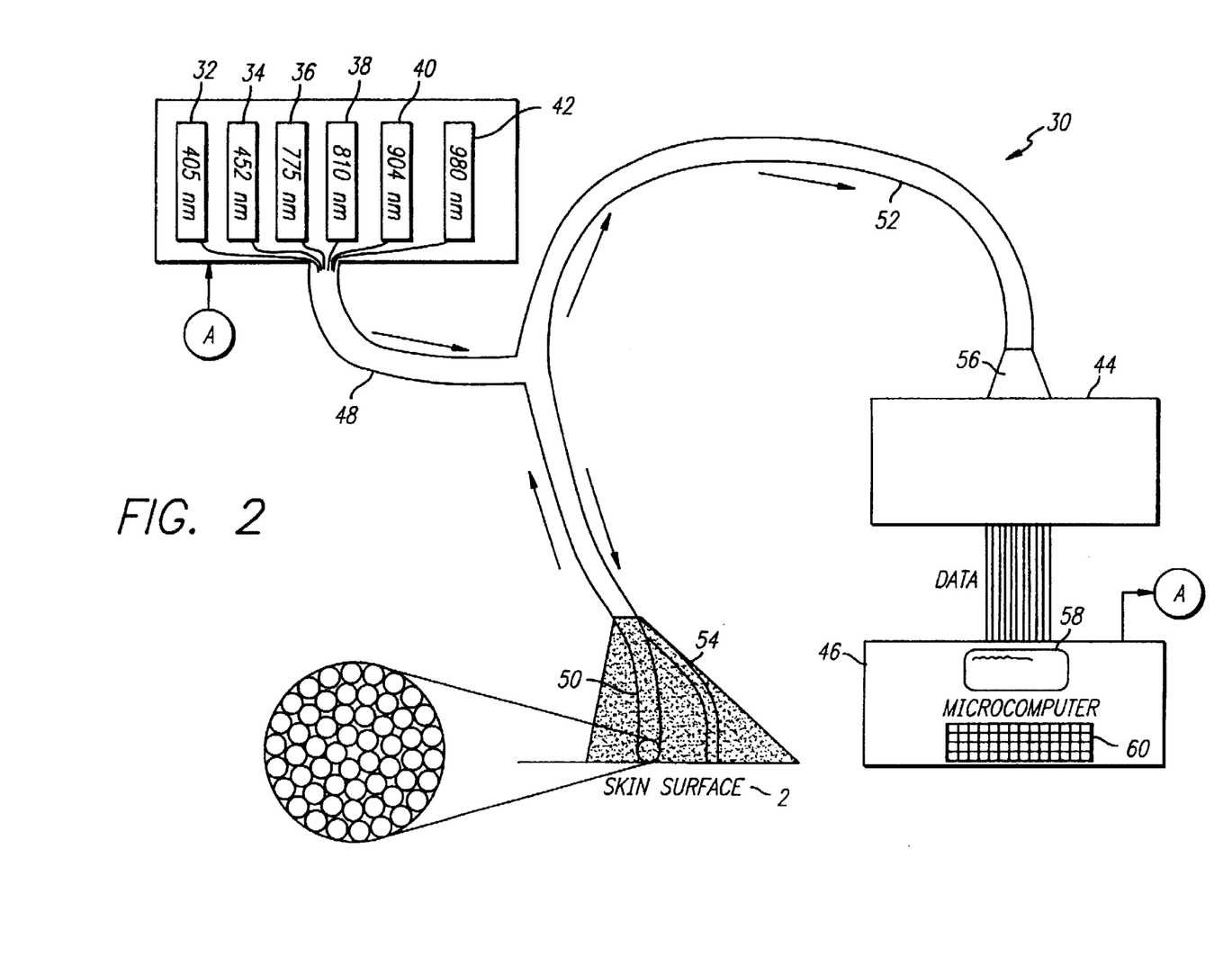
FIG. 2 is a block diagram of a burn evaluation apparatus embodying the present invention.

With reference now to FIG. 2, the apparatus 30 of the present invention is shown to include a plurality of light sources 32–42, a sensor 44, and a processor 46. In addition, optical fiber bundles 48–54 assist in directing excitation light from the light sources to the burn site on the skin 2 and return light from burn site to the sensor 44.

The plurality of light sources 32–42 consist of six-diode lasers, each producing excitation light at a predetermined wavelength. The first light source 32 emits narrow-band excitation light having a wavelength of approximately 405 nanometers produced by frequency doubling light from a diode laser having a wavelength of approximately 810 nanometers. The second light source 34 emits narrow-band excitation light having a wavelength of about 452 nanometers produced by frequency doubling light from a diode laser having a wavelength of about 904 nanometers. The wavelengths of the excitation light from the first and second light sources are chosen to induce a fluorescence response in the skin's metabolic and structural compounds, discussed in more detail below. The third, fourth, and fifth light sources 36–40 emit near-infrared (NIR) light at the wavelengths of 775 nanometers, 810 nanometer, and 904 nanometers, respectively, which are useful in detecting content of and state of hemoglobin in the skin. The sixth light source emits infrared light having a wavelength of approximately 980 nanometers that is used to evaluate the skin's tissue water content.

The sensor 44 includes a wavelength division multiplexer (WDM) 56 covering a wavelength spectrum from about 400 nanometers to about 1000 nanometers. The WDM images detected signals onto a linear 512 pixel charge-coupled device (CCD) array. The light exposure (light intensity x exposure time) for each pixel of the CCD array is digitized on a linear scale. The CCD array is cooled with a TE cooler or with liquid nitrogen to minimize background noise. Additionally, since the background noise signals are almost uniformly distributed across the array, the average noise signal may be subtracted from the signal from each detector element of the array. A suitable CCD array is the CCD- 512TKB thermoelectrically cooled CCD detector available from EG&G Princeton Applied Research of Princeton, N.J. The sensor provides the digitized signals from the CCD detector elements to the processor 46.

Preferably, the processor 46 is a microcomputer that performs the control and calculation functions of the present invention. The processor typically includes a color display 58 and a keyboard 60. A color display is advantageous for providing the surgeon with color-coded images of the analysis results. The processor 46 is programmed to control the sequencing and operation of the light sources 32–42 and the sensor 44 and stores the resulting signals.

The excitation light and return light are conveniently directed between the surface of the skin 2, the light sources, and the sensor by the optical fiber bundles 48–54. The main fiber bundle 50 is made of 200 to 400 individual optical fibers, each having a diameter of about 32 micrometers to 50 micrometers. The individual optical fibers are separated into 7 or 8 bundles of 30 to 50 optical fibers each bundle. Optical fibers from each light source form an excitation fiber bundle 48 that merges with the main fiber bundle. The remainder of the optical fibers (those not associated with a light source) form the detection fiber bundle 52 that directs the return light from the surface of the skin 2 to the sensor 44. The optical fibers from the excitation fiber bundle are randomly dispersed in the main fiber bundle to provide a uniform mix of excitation and detection fibers at the skin's surface. In addition to the main fiber bundle, a side fiber bundle 54 is provided at a distance of approximately 1 cm from the main fiber bundle 50. The side fiber bundle monitors deep reflectance (0.5 centimeters to 1 centimeter) of light from below the skin's surface. The side fiber bundle is used in conjunction with the 980 nanometer light source to monitor the amount of tissue water below the skin. A lens or lens system (such as a confocal lens configuration) may be included at the end of the fiber-optic bundles so that the bundles can operate as a non-contact probe.

Figure 3:
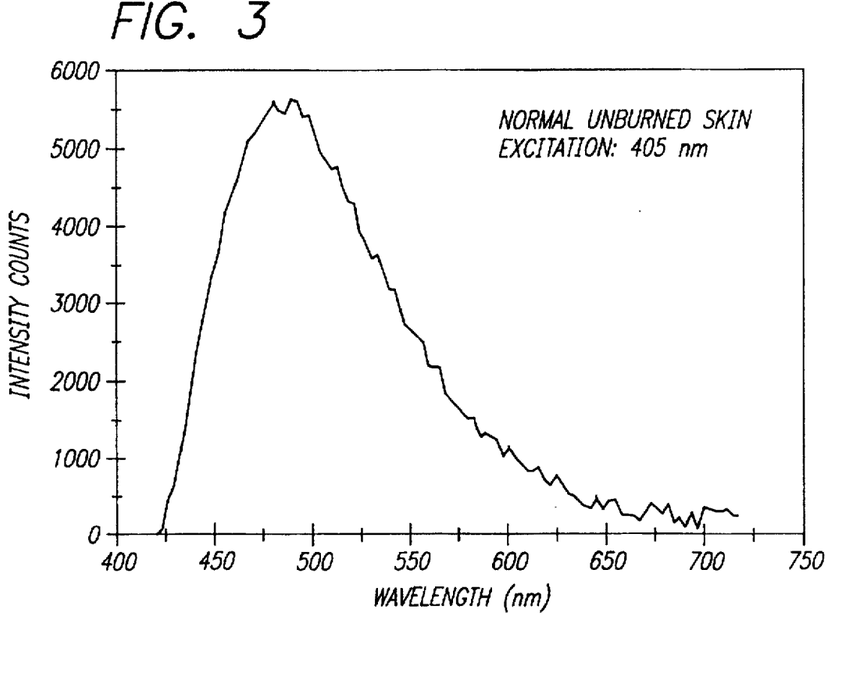
FIG. 3 is a graph prospectively representing the intensity of fluorescence verses wavelength for normal skin induced to fluoresce by laser light having a wavelength of about 405 nanometers.
Figure 4:
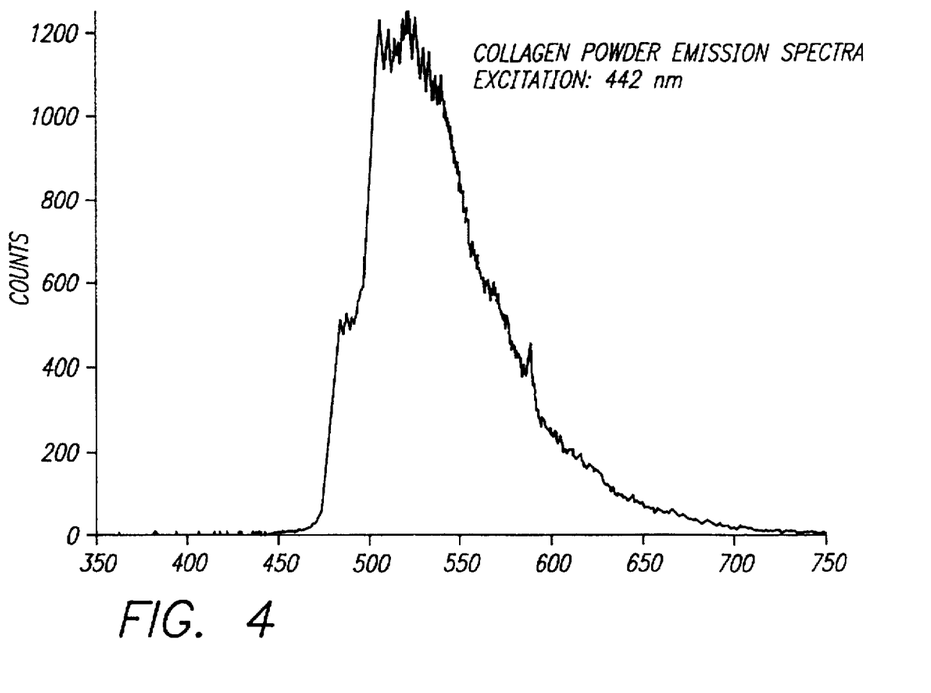
FIG. 4 is a is a graph of the intensity of fluorescence verses wavelength for collagen powder induced to fluoresce by laser light having a wavelength of about 442 nanometers.
Figure 5:
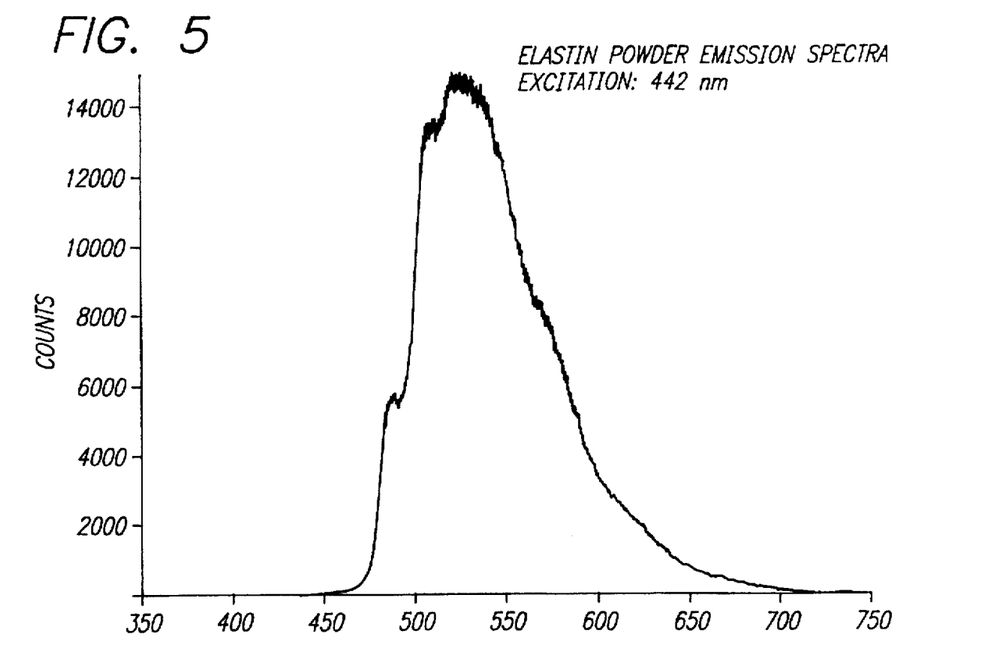
FIG. 5 is a graph of the intensity of fluorescence verses wavelength for elastin powder induced to fluoresce by laser light having a wavelength of about 442 nanometers.
Figure 6:
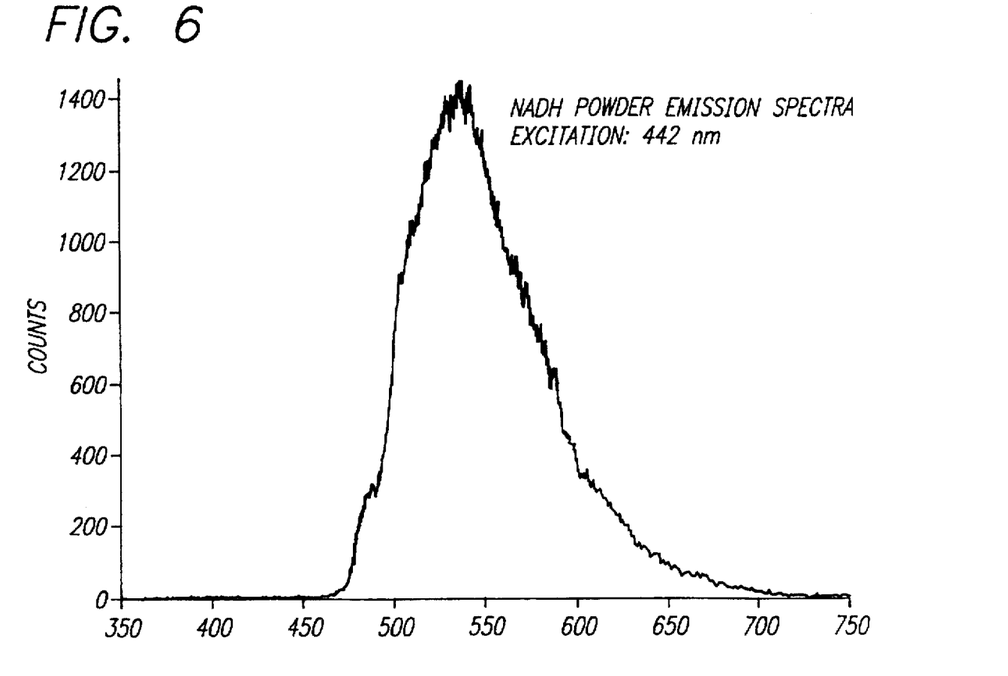
FIG. 6 is a graph of the intensity of fluorescence verses wavelength for NADH powder induced to fluoresce by laser light having a wavelength of about 442 nanometers.

The burn evaluation apparatus of the present invention takes advantage of the fact that the normal spectroscopic response of certain structural and metabolic constituents in the skin 2 are altered by a burn injury. More specifically, normal skin has a unimodal fluorescence response curve when induced to fluoresce by light having a wavelength of about 405 nanometers, reflected in the prospectively representative curve shown in FIG. 3. The curve is produced by induced fluorescence in certain naturally occurring fluorescent chemical compounds in the skin, namely, elastin, collagen, NADH, and FAD. The elastin and collagen relate to the structural condition of the skin and the NADH and FAD relate to the metabolic condition of the skin. As can be seen in FIGS. 4–7, each of these constituents contribute in varying amounts to the fluorescence spectrum measured in the skin. (It is noted that FIGS. 4–7 were produced using excitation light having a wavelength of about 442 nanometers. These curves would shift toward shorter wavelengths in response to excitation light having a wavelength of 405 nanometers.)

Figure 8:
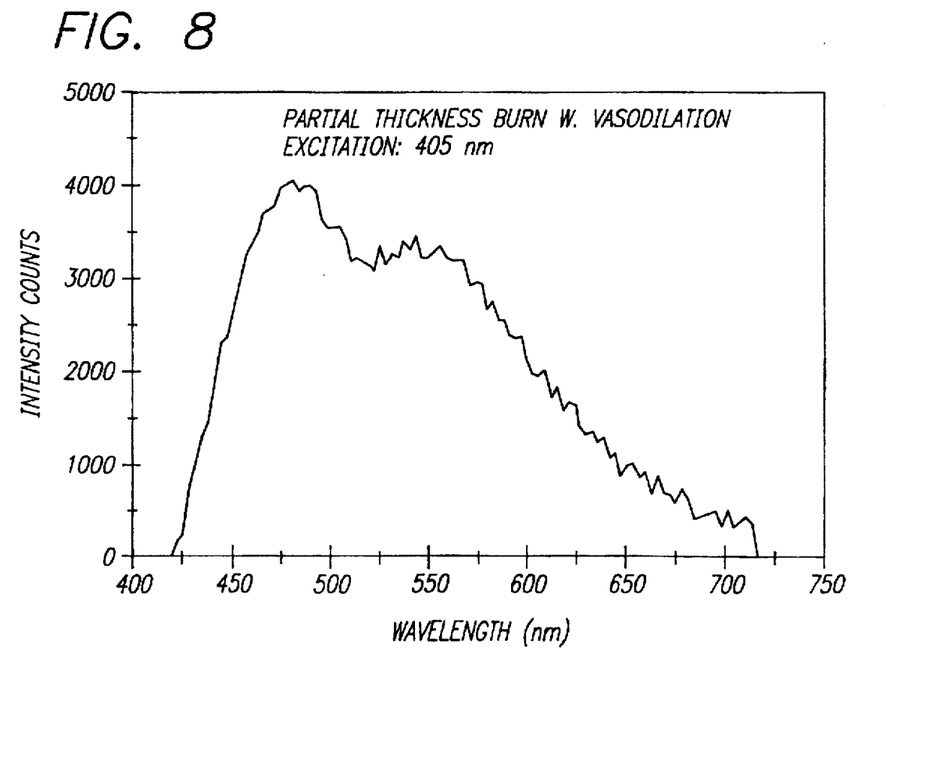
FIG. 8 is a graph prospectively representing the intensity of fluorescence verses wavelength for skin, having a partial thickness burn with vasodilation, induced to fluoresce by laser light having a wavelength of about 405 nanometers.
Figure 9:
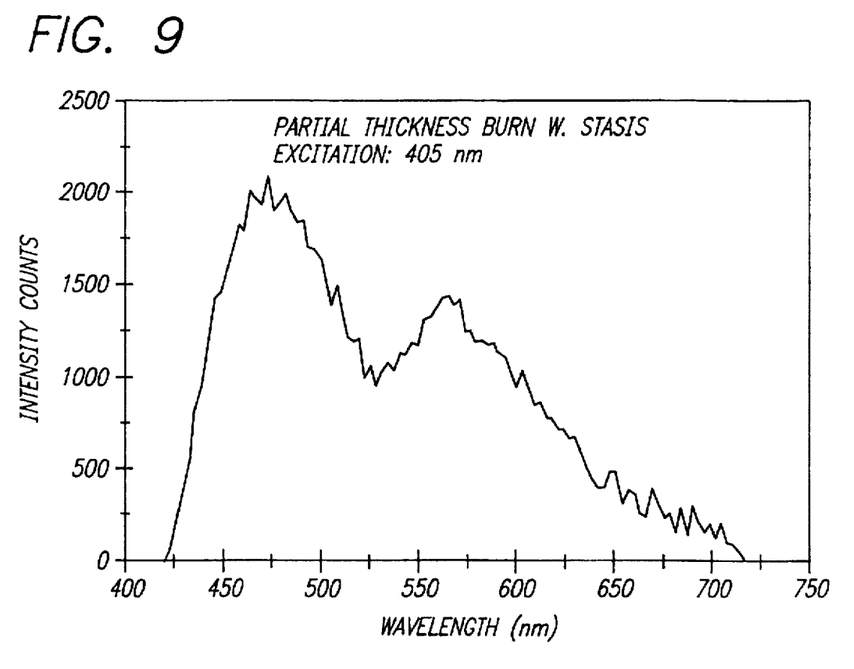
FIG. 9 is a graph prospectively representing intensity of fluorescence verses wavelength for skin, having a partial thickness burn with vascular stasis, induced to fluoresce by laser light having a wavelength of about 405 nanometers.
Figure 10:
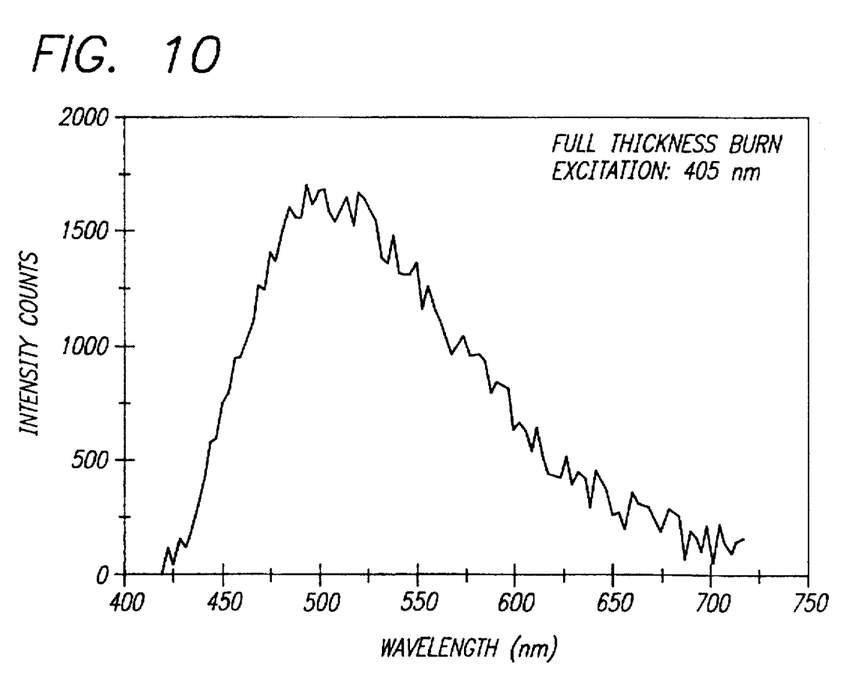
FIG. 10 is a graph prospectively representing intensity of fluorescence verses wavelength for skin having a full-thickness burn induced to fluoresce by laser light having a wavelength of about 405 nanometers.

However, after a superficial dermal burn, the blood vessels 14 dilate to promote healing, increasing the amount of hemoglobin in the area of the burn site. Since hemoglobin absorbs light having a wavelength between about 400 nanometers and about 500 nanometers, the fluorescence spectrum curve from skin 2 having a superficial dermal burn has a bimodal profile as shown in FIG. 8. After sufficient dermal heating, the blood vessels may be damaged resulting in vascular stasis. In this condition, the hemoglobin circulates poorly and any oxygenated hemoglobin tends to be eventually reduced. As shown in FIG. 9, the fluorescence spectrum curve has a more pronounced bimodal profile when vascular stasis occurs in the skin. In a full-thickness burn, the elastin, collagen, and other constituents of the skin have been severely altered or damaged and the profile of the fluorescence spectrum curve returns to a structureless unimodal shape as shown in FIG. 10. The surgeon often will not be confused by this profile since visual inspection will quickly reveal that the skin is not normal.

Figure 11:
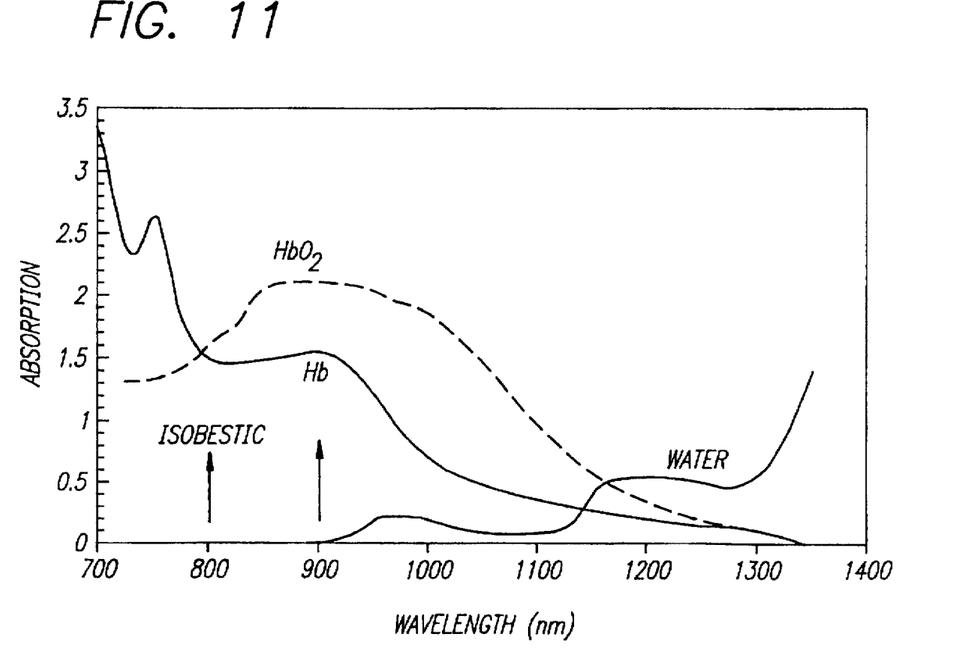
FIG. 11 is a graph indicating the absorption spectra of Hemoglobin (Hb), oxygenated hemoglobin ($HbO_2$), and water ($H_2O$).
Figure 12:
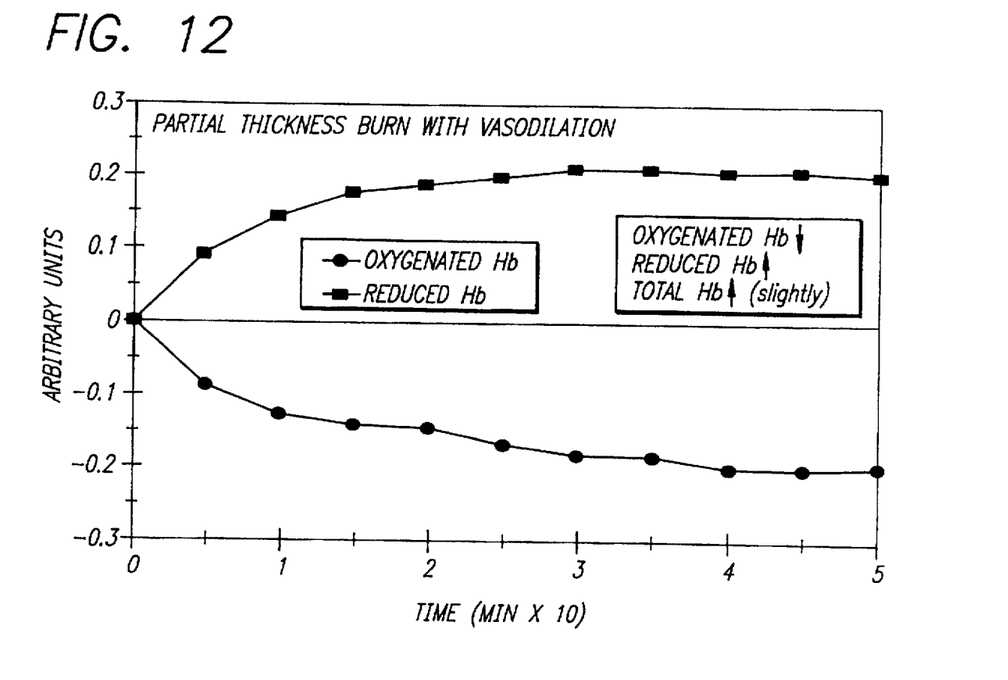
FIG. 12 is a graph prospectively representing relative amounts of oxygenated hemoglobin and reduced hemoglobin verses time for a partial-thickness skin burn with vasodilation.
Figure 13:
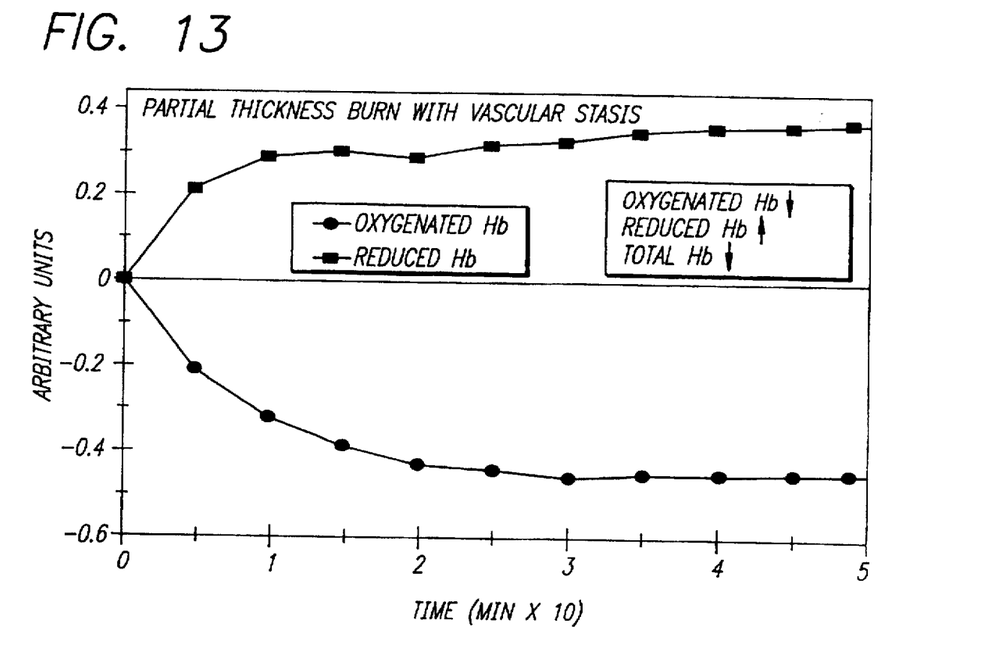
FIG. 13 is a graph prospectively representing relative mounts of oxygenated hemoglobin and reduced hemoglobin verses time for a partial-thickness skin burn with vascular stasis.

Although the bimodal curve for a burn with vascular stasis (FIG. 9) has more pronounced dip than the bimodal curve for a burn with vasodilation (FIG. 10), further confirmation of the condition of the skin at the burn site is evidenced by NIR absorption analysis of the hemoglobin present. As shown in FIG. 11, hemoglobin (Hb) and oxygenated hemoglobin ($HbO_2$) have distinct absorption (and reflection) profiles. Further, as shown by FIGS. 12 and 13, the total hemoglobin present in a burn site with vasodilation (FIG. 12) typically will be higher than the total hemoglobin present in a burn site with vascular stasis (FIG. 13). By measuring the reflectance of excitation light at the respective wavelengths of 775 nanometers, 810 nanometers, and 904 nanometers, the total amount of hemoglobin and relative amounts of oxygenated hemoglobin and reduced hemoglobin can be determined.

A further indication of the extent of burn injury is given by the water content of the skin 2 and the tissues below the skin. The water reflectance is measured using the light source providing light having a wavelength of 980 nanometers. At this wavelength, the absorption curve of water experiences a small peak (FIG. 11). The water content of the skin is monitored using the main fiber bundle 50 and the water content of the tissues below the skin are measured using the side fiber bundle 54. The side fiber bundle collects IR light emitted by the main fiber bundle and reflected by water in the tissues below the skin.

Figure 14:
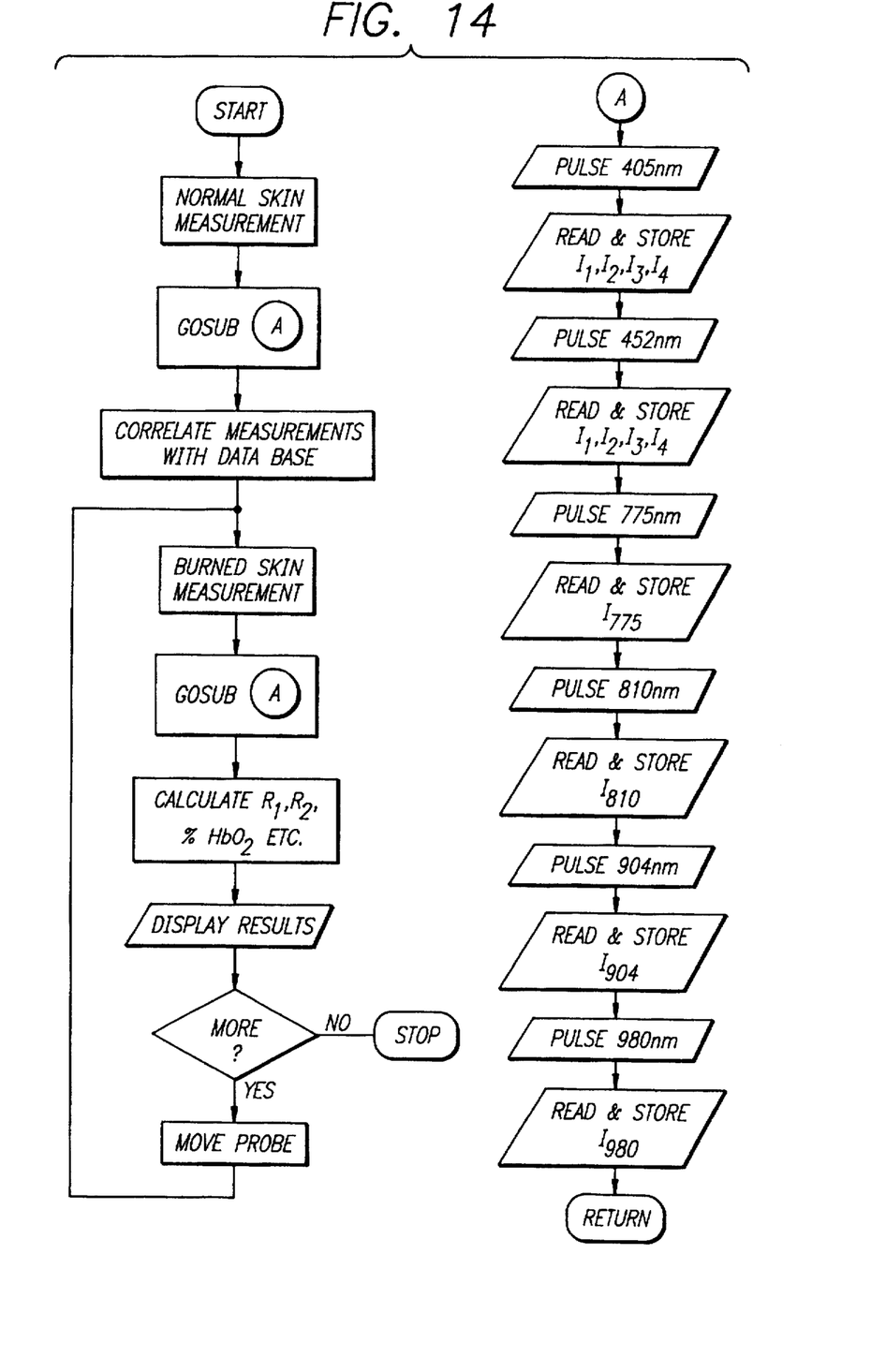
FIG. 14 is a flowchart indicating a method to be implemented by the burn evaluation apparatus of FIG. 2.
Figure 15:
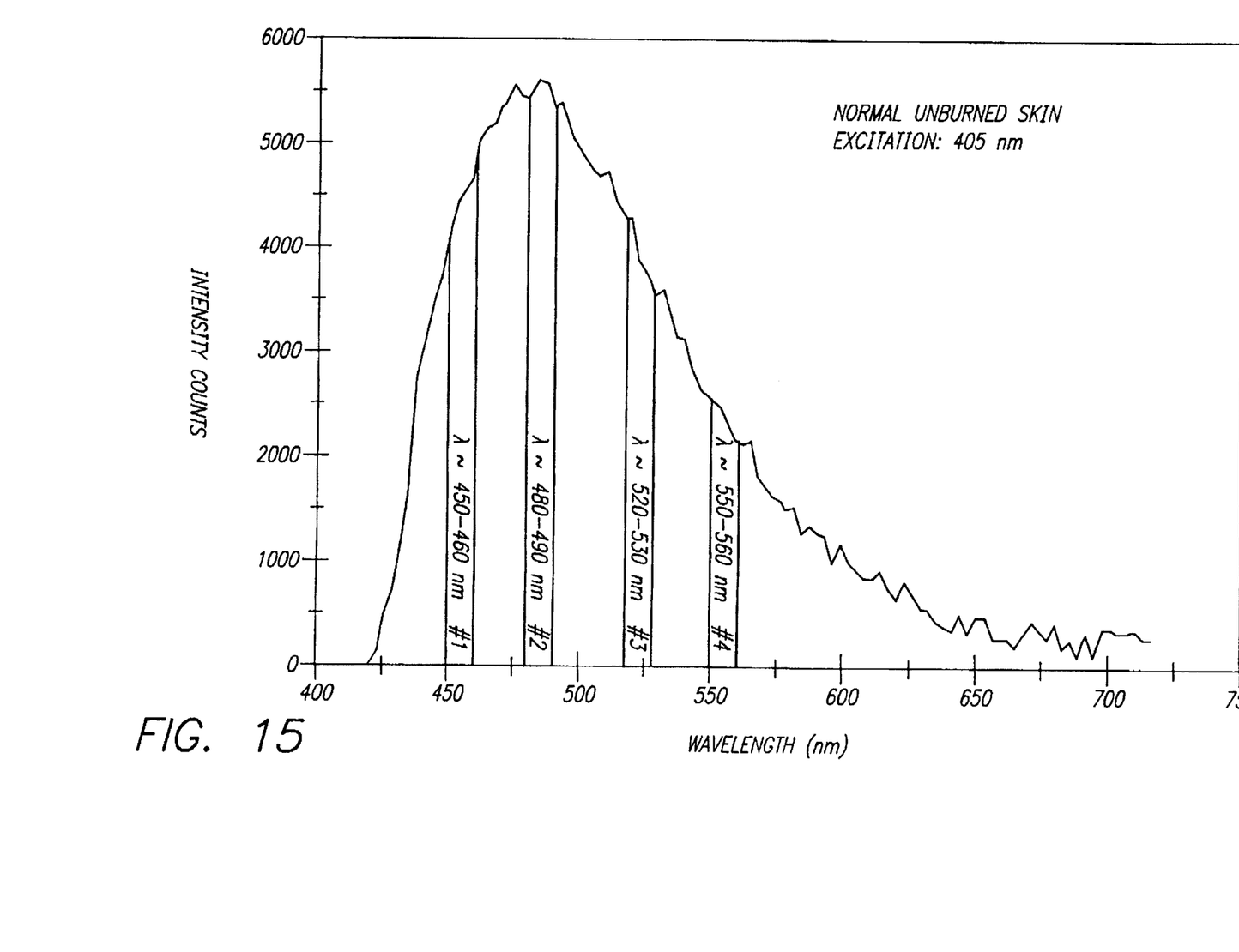
FIG. 15 is a graph prospectively representing intensity of fluorescence verses wavelength for normal skin (FIG. 3) overlaid by four predetermined wavelength bands.

The operation of the apparatus 30 is described with additional reference to FIGS. 14 and 15. The spectroscopic measurements preformed in evaluating skin burn injuries are largely influenced by the skin's melanin content, age, bodily location, etc. Therefore, before the apparatus evaluates the burned skin 2, the apparatus is "calibrated" by performing measurements on a similar area of normal unburned skin of the same individual. For example, if the individual is burned on the left shoulder, then the normal skin measurement would be performed on a similar location of the right shoulder. The measurement sequence for normal skin is similar to the measurement sequence for the evaluation of the burned skin, discussed below. The calibration measurements are compared against data in a database of normal skin measurements and a closest match is found. Each skin type in the database also includes associated empirical data relating to different degrees of burns for that skin type. Thus, by matching the normal unburned skin of the individual with a skin type in the database, the apparatus has available information regarding the spectroscopic characteristics of different degrees of burn injury to that skin type and, accordingly, is better able to evaluate the burn injury using the data from the database. Each burn injury evaluation provides further data that can be used to increase the number of skin measurements available in the database for performing the "calibration." Initially, the database may be derived from information in the published literature.

After the matching of the individuals normal skin 2 with the skin types in the database, the apparatus 30 is ready for evaluation of the burn injury. A probe, consisting of the main and side optical fiber bundles 50 and 54, is placed on the skin's surface in the area of the burn injury. The processor 46 activates the first laser 32, causing it to emit a pulse of excitation light having a wavelength of 405 nanometers, and enables the sensor 44 to receive any return light generated during a predetermined time interval. The excitation light is directed through the excitation fiber bundle 48 and the main fiber bundle to the site of the burn injury. Return light from the excited skin is collected from the burn site by the main fiber bundle and further directed to the sensor by the detection fiber-optic bundle 52. The sensor is activated to receive any return light only during the predetermined time interval. The return light received during the predetermined time interval presumably results from fluorescence induced by the 405 nanometer excitation light.

As discussed above, the sensor generates digitized signals representing the collected return light. The processor preferably, but not necessarily, selects four wavelength bands from the received digitized signals as shown in the prospectively representative graph of FIG. 15. The four wavelength bands each have a width of 10 nanometers and are centered around 455 nanometers, 485 nanometers, 525 nanometers, and 555 nanometers. For each of these wavelength bands, the area under the curve is computed, which represents the intensity of return light received in these wavelength bands.

The computer calculates two intensity ratios $R_1$ and $R_2$ from the area calculations of the four wavelength bands using the following formulas:

$$R_1 = I_3/I_2$$

and $$R_2 = I_1/I_4$$

where:

$I_1$, $I_2$, $I_3$, and $I_4$ are the intensity of return light measured in the four wavelength bands centered about 455 nanometers, 485 nanometers, 525 nanometers, and 555 nanometers, respectively. The values of these ratios $R_1$ and $R_2$ are used as indicators of the grade of thermal skin damage and are indicative of the contributions of elastin and collagen, and to a lesser extent, NADH and FAD, to the fluorescent spectra of the skin 2 when excited by light having a wavelength of 405 nanometers.

Continuing the evaluation, the processor 46 then activates the second laser 34, causing it to emit a pulse of excitation light having a wavelength of 452 nanometers, and enables the sensor 44 to receive return light. At this excitation wavelength, the processor selects four wavelength bands and again calculates two intensity ratios. The selected wavelength bands are shifted toward a longer wavelength (not shown) when compared to the previously selected wavelength bands (FIG. 15) as a result of using excitation light having a longer wavelength (452 nanometers). At this wavelength, the calculated intensity ratio are indicative of the contributions of NADH and FAD and, to a lesser extent elastin and collagen, to the fluorescent spectra of the skin.

The processor 46 then evaluates the NIR absorption (or reflectance) of the skin 2 by sequentially activating the next three lasers 36–40. For each wavelength, the processor enables the sensor 44 to receive the return light and monitors the reflected light having same wavelength as the selected laser. From the signals provided by the sensor, the processor computes the intensity of return light within a wavelength band centered about the wavelength of the respective light source. The processor then computes the logarithm of the measured intensity after each laser is activated. Using these computed values, the values measure for the healthy skin, and the empirical information from the database, oxygenated hemoglobin, reduced hemoglobin, and total hemoglobin content in the skin is determined by matrix inversion. Alternatively, a nonlinear optimization algorithm is used to minimize the quadratic error between observed and measured reflection (or absorption) levels. Both approaches utilize a empirically derived or known extinction coefficient for the compound of interest.

Finally, the sixth laser 42 is activated causing it to emit a pulse of excitation light having a wavelength of about 980 nanometers. The light received by the side fiber bundle 54 is monitored and the processor 46 calculates the return light received in a wavelength band centered about 980 nanometers. The side fiber is used to gain information about the tissue water content below the skin. By spacing the side fiber bundle about 1 centimeter from the main fiber bundle 50, reflected light from the first 0.5 centimeters below the skin's surface is avoided. Additionally, the tissue water of the skin can be monitored by performing this measurement using the main fiber bundle 50.

The values determined in the above evaluation of skin 2 damage for the investigated site is then provided to the surgeon and compared with the database of values experimentally obtained from different cases of thermal skin damage. The calculated values are displayed on the color display 58, as well as any graphs as desired by the surgeon. The time to complete the sequence can take only a few seconds allowing for almost immediate evaluation of the burn injury at the location of the probe. The surgeon can then probe other areas of the burned skin to evaluate the extent of the burn area. Further, the measurements can be stored in the processor 46 for comparison with later measurements to provide the surgeon with trend data that would further enable the surgeon to assess the viability of the burned skin.

Figure 7:
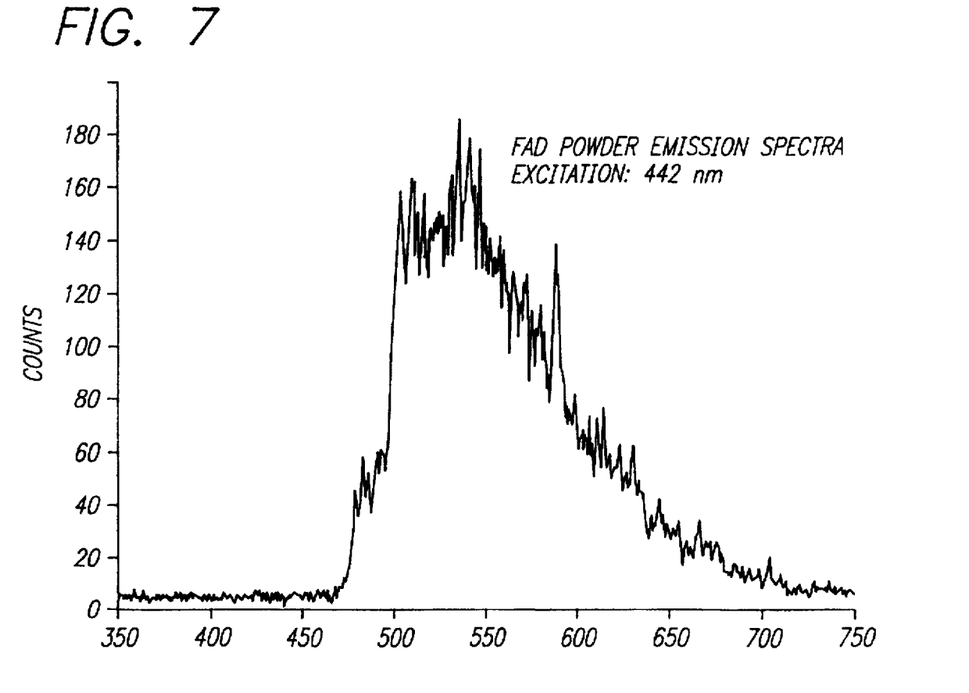
FIG. 7 is a graph of the intensity of fluorescence verses wavelength for FAD powder induced to fluoresce by laser light having a wavelength of about 442 nanometers.
Figure 16:
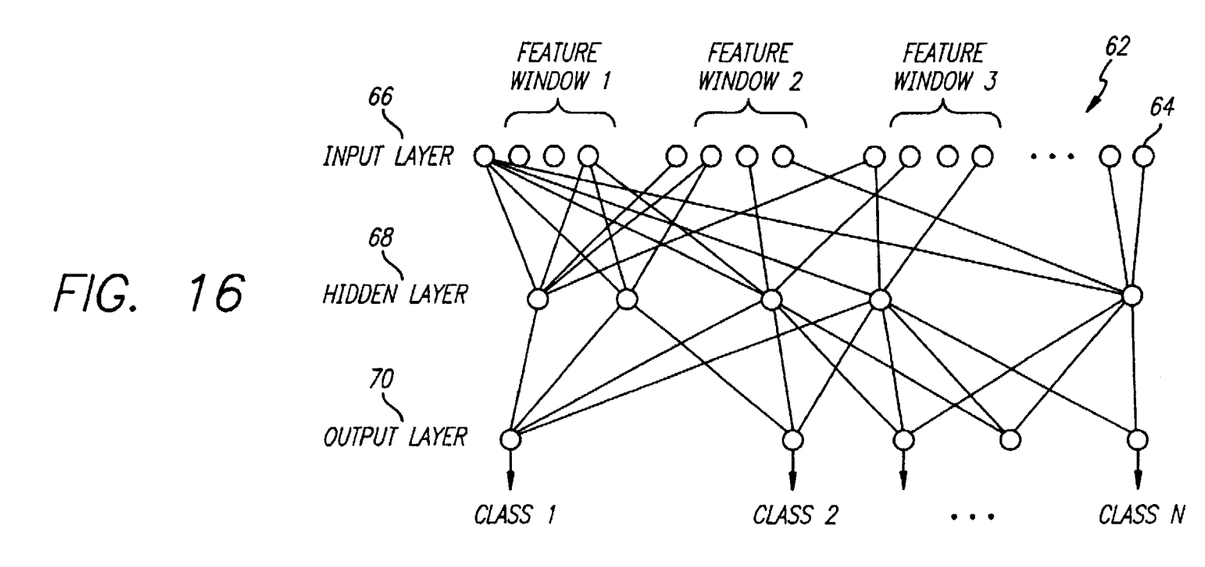
FIG. 16 is a schematic diagram of the concept of a neural network.
Figure 17:
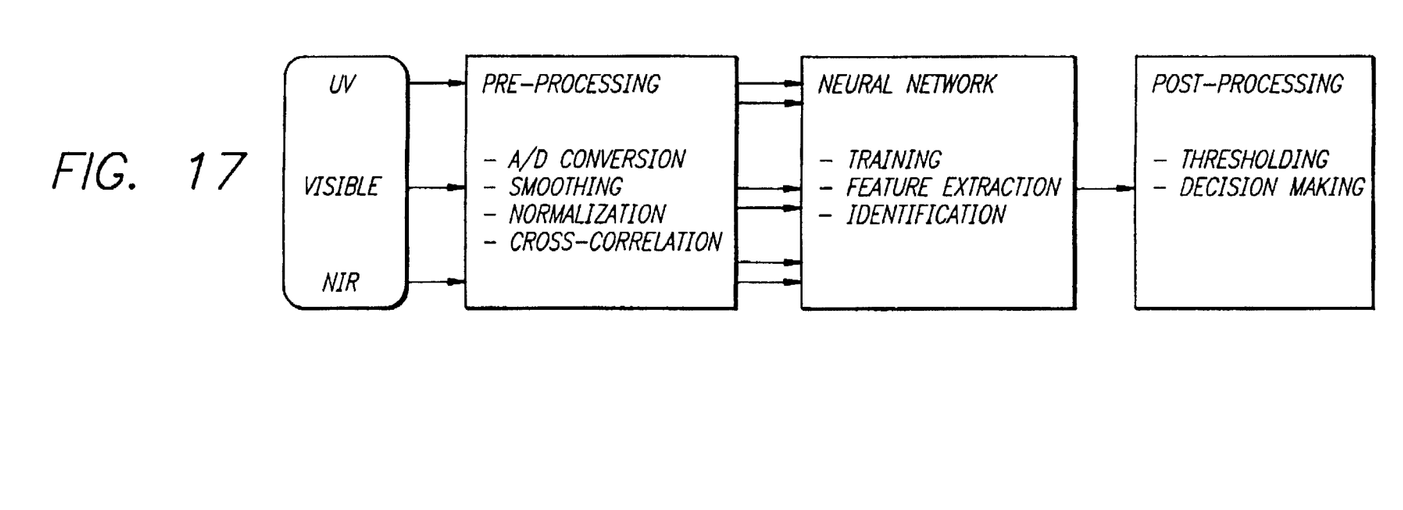
FIG. 17 is a block diagram of spectral signal processing algorithms for the neural network of FIG. 16.

In an alternative embodiment of the invention, the processor 46 may include an artificial neural network 62 as shown in FIGS. 16–17. The artificial neural network consists of layers of interconnected processors (neurons) 64. The spectral data from the processor 46 is input at input neuron layer 66. Preferably, each of the wavelength bands discussed above is divided into 10 smaller bands or windows. The input neuron layer has sufficient inputs to receive the data for each of the wavelengths of interest. The neural network performs a nonlinear transformation on the input data, using the hidden neuron layer 68, and produces its result at the output neuron layer 70'. Neural network has great flexibility in that it can be taught to transform the spectral data (input neuron layer) into an output (output neuron layer) that automatically and uniquely identifies the condition of a burn injury with extremely high sensitivity high speed (a fraction of a second for identifying one spectrum), and high reliability (confidence level being indicated by the neural network output) (FIG. 7). The software implementing the neuron network is preferably, but not necessarily, the substance identification "Neural Network" software package from Physical Optics Corporation of Torrance, Calif. The neural network operations and decision making may be performed on an IBM compatible personal computer.

Figure 18:
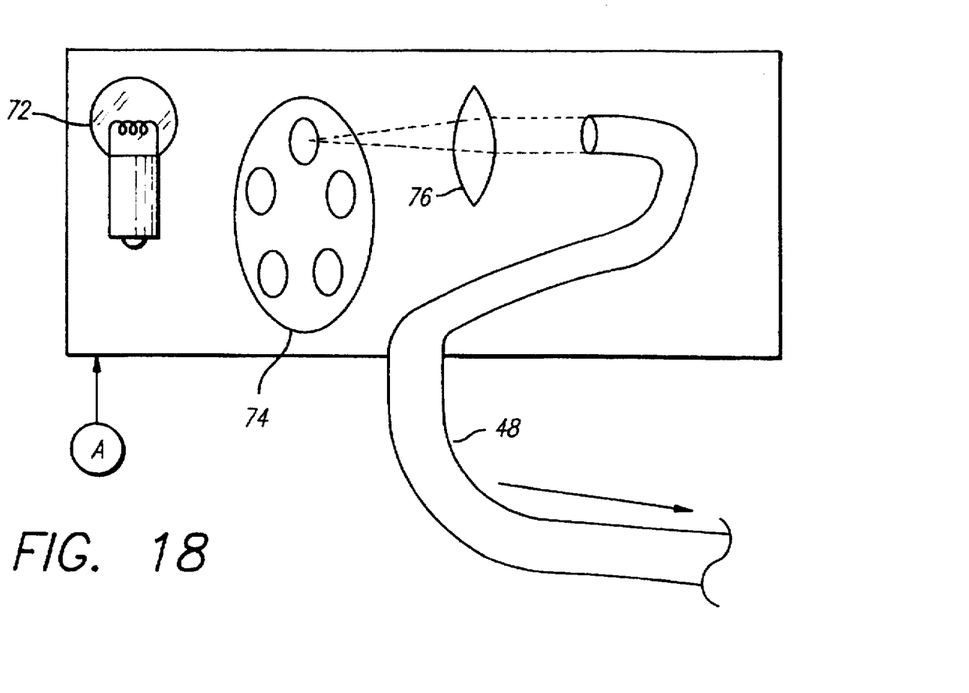
FIG. 18 is a block diagram of an alternative embodiment of a burn classification apparatus of the present invention.

In an alternative embodiment of the present invention, the plurality of light sources 32–42 are replaced by an arc lamp 72, filter wheel 74, and lens 76 as shown in FIG. 18. It will be readily recognized by one skilled in the art that the apparatus of the present invention can utilize a large variety of excitation wavelengths and monitored wavelength bands to evaluate a burn injury. The apparatus need not be limited to only six excitation wavelengths or any specific number of monitored wavelength bands.

Although the foregoing discloses preferred embodiments of the present invention, it is understood that those skilled in the art may make various changes to the preferred embodiment shown without departing from the scope of the invention. The invention is defined only by the following claims.

I claim:

1. Apparatus for evaluating the condition of burned skin at the site of the burn injury to the skin, comprising:
a plurality of light sources, each emitting excitation light having a predetermined wavelength, that is directed at the burn site to produce return light, wherein at least one light source is characterized by a wavelength of sufficient energy to cause fluorescence of certain chemical constituents of the skin and the return light includes fluorescent light produced by constituents present within the skin;
a sensor, responsive to the return light corresponding to each light source, that monitors the return light and generates a plurality of electrical signals based on the intensity of return light within predetermined wavelength bands; and
a processor associated with the sensor, that processes the plurality of electrical signals and determines the condition of the skin at the site of the burn injury.

2. Apparatus for evaluating a burn injury to skin as defined in claim 1, wherein the plurality of light sources include a first light source that emits narrow band excitation light having a wavelength between 300 nanometers and 480 nanometers.

3. Apparatus for evaluating a burn injury to skin as defined in claim 2, wherein the plurality of light sources includes a first light source that emits excitation light having a wavelength of 405 nanometers, a second light source that emits excitation light having a wavelength of 452 nanometers, a third light source that emits excitation light having a wavelength of 775 nanometers, a fourth light source that emits excitation light having a wavelength of 810 nanometers, a fifth light source that emits excitation light having a wavelength of 904 nanometers, and a sixth light source that emits excitation light having a wavelength of 980 nanometers.

4. Apparatus for evaluating a burn injury to skin as defined in claim 3, wherein each of the plurality of light sources includes a diode laser that generates the respective excitation light.

5. Apparatus for evaluating a burn injury to skin as defined in claim 3, wherein the plurality of light sources include a first light source producing light within a first wavelength band between 450 to 460 nanometers, a second light source producing light within a second wavelength band between 480 and 490 nanometers, a third light source producing light within a third wavelength band between 520 and 530 nanometers, a fourth light source producing light within a fourth wavelength band between 550 and 560 nanometers, a fifth light source producing light within a fifth wavelength band between 770 and 780 nanometers, a sixth light source producing light within a sixth wavelength band between 805 and 815 nanometers, a seventh light source producing light within a seventh wavelength band between 900 and 910 nanometers, and an eighth light source producing light within an eighth wavelength band between 970 and 990 nanometers.

6. Apparatus for evaluating a burn injury to skin as defined in claim 1, further comprising:
a first optical fiber bundle that includes
a plurality of excitation optical fibers, each excitation optical fiber associated with a respective light source to transmit excitation light from the light source to the site of the burn injury; and
one or more return optical fibers that transmit the return light from the site of the burn injury to the sensor.

7. Apparatus for evaluating a burn injury to skin as defined in claim 6, further comprising a second optical fiber bundle of one or more optical fibers that collect return light, the second bundle being located at a distance of approximately one centimeter from the first optical fiber bundle, during the evaluation of the burn injury.

8. Apparatus for evaluating a skin burn injury as defined in claim 1, wherein:
the plurality of light sources includes:
a first light source that emits excitation light having a wavelength not greater than about 480 nanometers to cause fluorescence of certain metabolic and structural constituents in the skin, and
a second light source that emits excitation light having a wavelength of at least about 772 nanometers to illuminate the hemoglobin at the burn injury site;
the return light includes light reflected by the hemoglobin present in the skin; and
the processor determines the potential viability of the skin at the site of the burn injury.

9. Apparatus for evaluating a skin burn injury as defined in claim 8, further comprising a display that provides an image that indicates the potential viability of the skin at the site of the burn injury.

10. Apparatus for evaluating a skin burn injury as defined in claim 8, wherein the plurality of light sources further includes a third light source having a wavelength of at least 980 nanometers to illuminate the water content of the skin and the return light includes light reflected by water present within the skin.

11. Apparatus for evaluating a skin burn injury as defined in claim 1, wherein:
the plurality of light sources includes a light source that emits, at a first location, excitation light having a wavelength of about 980 nanometers;
the sensor further monitors the return light at a second location situated approximately one centimeter from the first location and generates a first electrical signal based on the intensity of return light within a relatively based on the intensity of return light within a relatively narrow wavelength band centered at about 980 nanometers; and
the processor further processes the first electrical signal to evaluate the water content of the skin and tissues below the site of the burn injury.

12. Apparatus for evaluating a skin burn injury as defined in claim 1, wherein:
the sensor includes an optical probe for monitoring the reflectance of infrared light from below a surface of the skin at the site of the burn injury, the optical probe comprising:
a main optical fiber bundle that directs infrared light toward the surface, and
a side optical fiber bundle that is located approximately one centimeter from the main fiber bundle and that collects infrared light reflected from below the surface.

13. Apparatus for evaluating a skin burn injury as defined in claim 1, wherein:
the processor provides a database that associates, for a particular skin type, the fluorescence and spectroscopic characteristics of different degrees of burn injury occurring to the skin of the particular skin type; and the processor determines the condition of the skin at the site of the burn injury by

- determining the fluorescence and spectroscopic characteristics of the injured individual's normal skin,
- comparing the fluorescence and spectroscopic characteristics of the injured individual's normal skin with the fluorescence and spectroscopic characteristics of normal skin for the particular skin types in the database and selecting the closest match between the individual's skin type and the skin types provided in the database,
- obtaining from the database, information regarding the fluorescence and spectroscopic characteristics associated with different degrees of burn injury for the selected skin type for use in evaluating the degree of the individual's burn injury;
- determining the fluorescence and spectroscopic characteristics of the injured individual's burned skin;
- comparing the information obtained from the database for the selected skin type with the characteristics of the injured individual's burned skin to estimate the degree of burn injury of the burned skin; and
- indicating the estimated degree of burn injury of the injured individual's burned skin.

14. Apparatus for evaluating a skin burn injury as defined in claim 1, wherein:

- the plurality of light sources includes:
  - a first light source that emits excitation light having a wavelength between 300 and 480 nanometers to cause fluorescence of certain metabolic and structural constituents in the skin, and
  - a second light source that emits excitation light having a wavelength at about 775, 810 or 904 nanometers to illuminate the hemoglobin at the burn injury site;
- the return light includes light reflected by the hemoglobin present in the skin; and
- the processor determines the potential viability of the skin at the site of the burn injury.

15. Apparatus for evaluating a skin burn injury as defined in claim 14, wherein the plurality of light sources further includes a third light source having a wavelength of about 980 nanometers to illuminate the water content of the skin and the return light includes light reflected by water present within the skin.

* * * * *

UNITED STATES PATENT AND TRADEMARK OFFICE
CERTIFICATE OF CORRECTION

PATENT NO. : 5,701,902
DATED : December 30, 1997
INVENTOR(S) : S. Bari, et. al.

It is certified that error appears in the above-identified patent and that said Letters Patent is hereby corrected as shown below:

Col. 10, line 19, "about 772 nanometers" should read --about 775 nanometers--.

Signed and Sealed this

Second Day of June, 1998

Attest:

BRUCE LEHMAN

Attesting Officer

Commissioner of Patents and Trademarks